United States Patent [19]

Keimel

[11] Patent Number: 5,188,105
[45] Date of Patent: Feb. 23, 1993

[54] APPARATUS AND METHOD FOR TREATING A TACHYARRHYTHMIA

[75] Inventor: John G. Keimel, New Brighton, Minn.

[73] Assignee: Medtronic, Inc., Minneapolis, Minn.

[21] Appl. No.: 612,761

[22] Filed: Nov. 14, 1990

[51] Int. Cl.$^5$ .............................................. A61N 1/39
[52] U.S. Cl. ................................................ 128/419 D
[58] Field of Search ................................... 128/419 D

[56] References Cited

U.S. PATENT DOCUMENTS

| | | | |
|---|---|---|---|
| Re. 27,757 | 3/1987 | Mirowski | 128/419 D |
| 3,236,239 | 2/1966 | Berkovits | 128/419 D |
| 3,527,228 | 9/1970 | McLaughlin | 128/419 D |
| 3,566,876 | 3/1971 | Stoft et al. | 128/421 |
| 3,738,370 | 6/1973 | Charms | 128/419 D |
| 4,384,585 | 5/1983 | Zipes | 128/419 D |
| 4,572,191 | 2/1986 | Mirowski et al. | 128/419 D |
| 4,787,389 | 11/1988 | Tarjan | 128/419 D |
| 4,949,719 | 8/1990 | Pless et al. | 128/419 D |
| 5,007,422 | 4/1991 | Pless et al. | 128/419 D |

OTHER PUBLICATIONS

Ventak® PRX ™ Model 1700 Automatic Implantable Cardioverter Defibrillator, Physician's Manual.
Technical Manual "The PCD ™ Tachyarrhythmia Control Device" Model 7216A.

*Primary Examiner*—William E. Kamm
*Assistant Examiner*—Scott M. Getzow
*Attorney, Agent, or Firm*—Harold R. Patton; Reed A. Duthler

[57] ABSTRACT

An implantable cardioverter/defibrillator capable of detecting fibrillation and other tachyarrhythmias and of generating high energy cardioversion and defibrillation pulses. The device delivers cardioversion pulses and defibrillation pulses synchronized to heart rhythm, wherever possible. Delivery of cardioversion pulses requires verification of the continuing presence of a tachyarrhythmia, following charge up of the output capacitor in the pulse generator. In the event that cardioversion therapy is aborted, the charge on the capacitor is retained until subsequent detection of termination of the tachyarrhythmia. Defibrillation pulses are delivered synchronized to heart rhythm, wherever possible, but are delivered asynchronously if synchronization is not possible. Following delivery of a cardioversion or defibrillation pulse, the charge remaining on the capacitor is retained until detection of tachyarrhythmia or fibrillation termination, respectively.

12 Claims, 12 Drawing Sheets

APPARATUS AND METHOD FOR TREATING A TACHYARRHYTHMIA

BACKGROUND OF THE INVENTION

This invention relates generally to implantable medical stimulators, and more particularly to implantable cardioverters and defibrillators.

It has been known for some time that delivery of cardioversion and defibrillation pulses should be synchronized to the patient's own cardiac rhythm, if possible. For example, early synchronized cardioverters and defibrillators are disclosed in U.S. Pat. No. 3,236,239, U.S. Pat. No. 3,527,228, U.S. Pat. No. 3,566,876 and U.S. Pat. No. 4,572,191. All of these references disclose manually triggered synchronized cardioverters. Since that time, the art has progressed substantially, and includes numerous examples of automatically triggered, synchronized cardioverters. Such devices are disclosed in U.S. Pat. No. 3,738,370 issued to Charms et al. and in U.S. Pat. No. 4,384,585, issued to Zipes. Another example of such a deice is the Medtronic Model 7210 implantable cardioverter, which also automatically delivered synchronized cardioversion energy directly to the heart.

In implantable cardioverters, cardioversion and defibrillation pulses are generally delivered from capacitors, which are charged in response to the sensing of a tachyarrhythmia. In the device disclosed in Reissue U.S. Pat. No. 27,757, issued to Mirowski, the heart rhythm is monitored during charging of the output capacitors, and delivery of a cardioversion or defibrillation shock is aborted in the event that the heart returns to a normal sinus rhythm, during capacitor charging. However, most modern implantable cardioverters do not have the capability of sensing the heart's activity during charging of the capacitors. Some such devices, such as the Model 7210 impantable cardioverter discussed above, define a synchronization interval following capacitor charging and abort delivery of the cardioversion pulse if no R-wave is sensed during this interval. An additional approach is embodied in the Ventritex Cadance ™ defibrillator, which monitors the heart's rhythm during charging of the capacitors, aborting the charging sequence and the delivery of defibrillation or cardioversion pulses in the event that continued presence of tachyarrhythmia is not verified. The Ventritex device also apparently checks the cardiac rhythm after charging, as a prerequisite to delivery of synchronized cardioversion pulses, and aborts delivery of cardioversion pulses in the event that continuing presence of the tachyarrhythmia cannot be confirmed.

SUMMARY OF THE INVENTION

The present invention is directed towards a synchronous cardioverter which employs an improved method of synchronization. In the case of cardioversion pulses intended to terminate ventricular tachycardias, the synchronization method also provides an abbreviated method for reconfirmation of the presence of the tachycardia as a prerequisite to delivery of the cardioversion shock. In response to detection of ventricular fibrillation, an attempt is made to synchronize defibrillation shock, with the shock provided asynchronously if synchronization cannot quickly be accomplished.

In response to detection of ventricular tachycardia, the cardioverter charges its output capacitors, and defines sequential synchronization intervals. Each synchronization interval includes a blanking period, at the beginning of the synchronization interval, during which the device does not respond to ventricular depolarizations or R-waves. Each synchronization interval also includes a refractory interval, extending from the beginning of the synchronization interval, and extending past the end of the blanking interval. A portion of the refractory interval which follows the blanking interval functions as a noise sensing interval.

Cardioversion shocks are delivered only in response to the sensing of R-waves in the post-refractory portions of two sequential synchronization intervals, with the cardioversion shock synchronized to the second such R-wave. This assures continued presence of the tachyarrhythmia as a prerequisite to delivery of the cardioversion shock.

In the event that an R-wave is sensed during the refractory period, after the blanking period, the next synchronization interval is initiated. If R-waves are sensed in the refractory intervals of three successive synchronization intervals, cardioversion therapy is aborted. This aspect of the synchronization method avoids delivery of cardioversion pulses in cases where it is likely that repetitive electrical noise has resulted in the erroneous detection of a tachyarrhythmia or in which synchronization is rendered impossible due to repetitive noise.

In the event that an entire synchronization interval passes without the sensing of an R-wave therein, the cardioversion therapy is also aborted. This aspect of the synchronization method addresses situations in which the tachycardia has spontaneously terminated during or shortly after completion of capacitor charging.

In all cases in which cardioversion therapies are aborted, the device returns to a VVI mode, bradycardia pacing therapy. However, the output capacitors remain charged, and are not discharged thereafter until detection of tachycardia termination, typically accomplished by means of detection of a predetermined number of R-R intervals greater than a predetermined duration. This feature of the synchronization method allows for rapid delivery of a cardioversion pulse in the event that the cessation of the sensed tachyarrhythmia was only temporary, without the necessity of recharging the capacitors. This feature is valuable to limit the drain on the battery due to recharging of the capacitors.

In response to detection of ventricular fibrillation, the output capacitors are similarly charged, with the defibrillation pulse synchronization procedure initiated thereafter. The defibrillation pulse synchronization method also provides for sequential synchronization intervals. The first interval includes both blanking and refractory periods corresponding to those discussed above in conjunction with the synchronization intervals for cardioversion therapy. The second synchronization interval includes a blanking interval, but not a refractory interval. Sensing of an R-wave during the refractory portion of the first synchronization interval initiates timing of the second synchronization interval. The remainder of the synchronization methodology, however, differs substantially from that described above.

Delivery of a defibrillation pulse occurs on the earliest of: a sensed R-wave i the post-refractory portion of the first synchronization interval; time-out of the first synchronization interval; occurrence of a sensed R-wave during the post-blanking portion of the second synchronization interval; or time-out of the second synchronization interval. As such, the defibrillation pulse synchronization method attempts to synchronize the deliver of the pulse to the heart activity. However, if this is not quickly possible, the device delivers an asynchronous defibrillation pulse with an interval of at least one synchronization period from the last R-wave which is considered a safe period of time for delivery of a therapy without the high probability of accelerating the rhythm. This approach differs from that taken in conjunction with the tachycardia synchronization algorithm, in that it treats cessation of sensed R-waves after sensing of fibrillation as indicative of fibrillation which produces electrical signals below the detection threshold of the sense amplifier, rather than indicative of a spontaneous return to sinus rhythm.

After delivery of either a cardioversion or defibrillation pulse, there is generally some voltage remaining on the output capacitors. As in the case in which delivery of cardioversion therapy is aborted, this voltage is not internally discharged until detection of termination of tachyarrhythmia or fibrillation. As discussed above, delaying the discharge of the remaining charge on the capacitors allows for a faster response upon redetection of tachycardia or fibrillation and reduces current drain on the batteries.

DETAILED DESCRIPTION OF THE PREFERRED EMBODIMENTS

Figure 1:
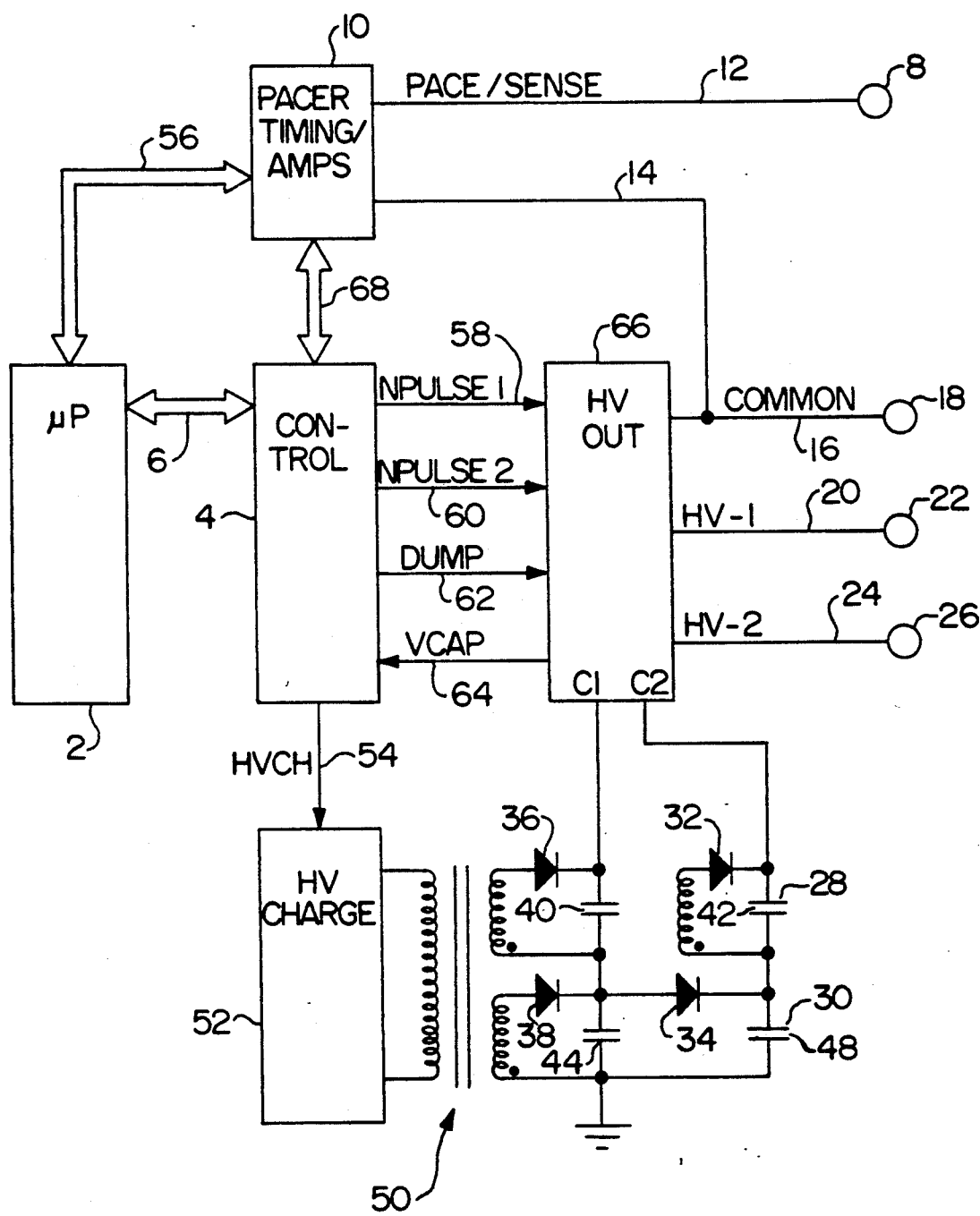
FIG. 1 is a block, functional diagram of an implantable pacemaker/cardioverter/defibrillator adapted to perform the synchronization methodology of the present invention.

FIG. 1 is a block, functional diagram illustrating an implantable pacemaker/cardioverter/defibrillator embodying the present invention. The device includes a microprocessor 2, which holds a stored program controlling the operation of the device. Microprocessor 2 includes a read-only memory, containing the firmware controlling the basic operation of the device, a random access memory, for storing measured parameters and for storing instructions related to variable operating procedures within the device, and also includes an arithmetic logic unit enabling the microprocessor to calculate the various time periods required by the device.

The second major block of the device is the control block 4, which serves to control operation of the high voltage output stage 66, which controls delivery of high energy cardioversion and defibrillation pulses to the electrodes 18, 22 and 26. Control signals and information pass between microprocessor 2 and control block 4 by means of a bi-directional data/control bus 6. Depending upon the particular pulse regimens programmed, microprocessor 2 enables control block 4 to trigger the delivery of the cardioversion and/or defibrillation pulses of the desired amplitude and pulse configuration. The interrelation of control circuitry 4 with high voltage output circuitry 66 is discussed in more detail and co-pending, commonly assigned patent application Ser. No. 07/612,761, for an "Apparatus for Delivering Single and Multiple Cardioversion and Defibrillation Pulses", filed as of the date of this application by Keimel. This application is incorporated herein by reference in its entirety. However, for the sake of the present application, it is believed sufficient to note that in response to a logic signal on signal NPULSE 1 line 58, capacitors 40 and 44 are discharged between electrodes 18 and 22, while in response to a logic signal on NPULSE 2 line 60, capacitors 40, 42, 44 and 48 are discharged through electrodes 18 and 26. The signals on NPULSE-1 line 58 and NPULSE-2 line 60 may be provided sequentially, simultaneously or individually.

Control block 4 also provides a signal on HVCH line 54 initiating the high voltage charging circuitry 52, during which the capacitors 40, 42, 44 and 48 are charged by means of high voltage transformer 50. Proper charging polarity is maintained by diodes 32, 34, 36 and 38. VCAP line 64 from high voltage output circuitry 66 provides a measurement of the voltage stored on the capacitors 40, 42, 44 and 48 to the control circuitry 4, so that it may terminate charging of the capacitors by means of HVCH line 54, when their voltage equals the voltage selected by microprocessor 2. Dump line 62 from control block 4 initiates discharge of capacitors 40, 42, 44 and 48 through an internal resistance, under the circumstances described below. Again, the operation of the high voltage output circuitry in conjunction with the output capacitors 40, 42, 44 and 48 is described in detail in the above-cited Keimel application. For purposes of the present application, however, it is believed sufficient to note that the signal on VCAP line 64 reflects the voltage stored on capacitors 40 and 44, and that the Dump line 62 initiates discharge of all four capacitors.

The device also includes cardiac pacemaker circuitry 10, which includes circuitry employed to control timing of cardiac pacing, an R-wave sense amplifier for detection of ventricular depolarizations via electrodes 8 and 18 and an output circuit for delivering cardiac pacing pulses between electrodes 8 and 18.

The R-wave amplifier employed in pacer circuitry 10 may be an amplifier according to U.S. Pat. No. 5,117,824, issued May 2, 1992, for an "Apparatus for Monitoring Electrical Physiological Signals" filed by Keimel et al., as of the date of the present application and incorporated herein by reference in its entirety. While this type of amplifier is believed particularly valuable in the context of an implantable pacemaker/cardioverter/defibrillator, other R-wave amplifiers known to the art may also be employed. Signals indicative of the occurrence of sensed R-waves and of cardiac pacing pulses are provided to control circuitry 4, via bi-directional bus 68.

The basic operation of the device is controlled by microprocessor 2, in conjunction with pacer circuitry 10 and control block 4. Pacer circuitry 10 includes a plurality of counters which time intervals associated with the bradycardia pacing. These intervals include a bradycardia pacing escape interval, representing the interval between successive cardiac pacing pulses and between sensed R-waves and the next subsequent cardiac pacing pulses. At the expiration of the brady pacing escape interval, a ventricular pacing pulse is delivered between electrodes 8 and 18. In response to sensing of an R-wave, the brady escape interval is re-initiated. Pacer circuitry 10 also defines a blanking period, during which R-waves are not sensed by the R-wave amplifier in pacer circuitry 10 and a refractory period, during which R-waves are sensed, but are ineffective to re-initiate timing of the brady pacing escape interval. Signals indicative of the occurrence of sensed R-waves and cardiac pacing pulses are passed to processor 2 as interrupts, awakening the microprocessor and allowing it to perform any necessary calculations. Microprocessor 2 controls the values timed by the timers in pacer circuitry 10 by means of control/data bus 56.

R-waves sensed by pacer timing/amplification block 10 are also employed by microprocessor 2 in performing tachycardia and fibrillation detection. Tachycardia and fibrillation detection algorithms believed appropriate for use in conjunction with the present invention are disclosed in the article "Onset and Stability for Ventricular Tachyarrhythmia Detection in an Implantable Pacer-Cardioverter Defibrillator" by Olson et al., published in Computers in Cardiology, Oct. 1986, pages 167-170 and incorporated herein by reference in its entirety. However, the present invention is also believed workable in conjunction with any of the numerous alternative fibrillation and tachycardia detection algorithms known to the art, including those disclosed in U.S. Pat. No. 4,548,209 issued to Wielders et al., U.S. Pat. No. 4,693,253 issued to Adams, U.S. Pat. No. 4,384,585 issued to Zipes, and U.S. Pat. No. 4,830,006 issued to Haluska et al., all of which are incorporated herein by reference in their entirety.

Microprocessor 2 also responds to interrupts indicating the occurrence of sensed R-waves to determine whether previously sensed fibrillation or tachycardias have terminated. In the context of the present invention, it is suggested that termination of tachycardia be verified by the sensing of a sequence R-R intervals (intervals separating R-waves), each of which exceeds a predetermined tachycardia detection interval. Detection of fibrillation determination may also be accomplished by means of the detection of a predetermined number of R-R intervals, all having durations in excess of a predetermined fibrillation detection interval. However, other termination detection methods are also believed workable in the context of the present invention.

Basic operation of the invention can be understood by reference to the flow charts illustrated in FIGS. 9 through 12. These flow charts are intended to reflect the overall function of the device, rather than any particular software or firmware which must be employed in the device. Because the invention is not dependent upon any particular software or firmware configuration in order to be practiced, the flow charts illustrated focus on the important functional aspects of the synchronization method, and their interrelation to an implantable pacemaker/cardioverter/defibrillator which includes fibrillation and tachycardia detection function and appropriate hardware for initiation of pacing, cardioversion and defibrillation pulses.

Figure 9:
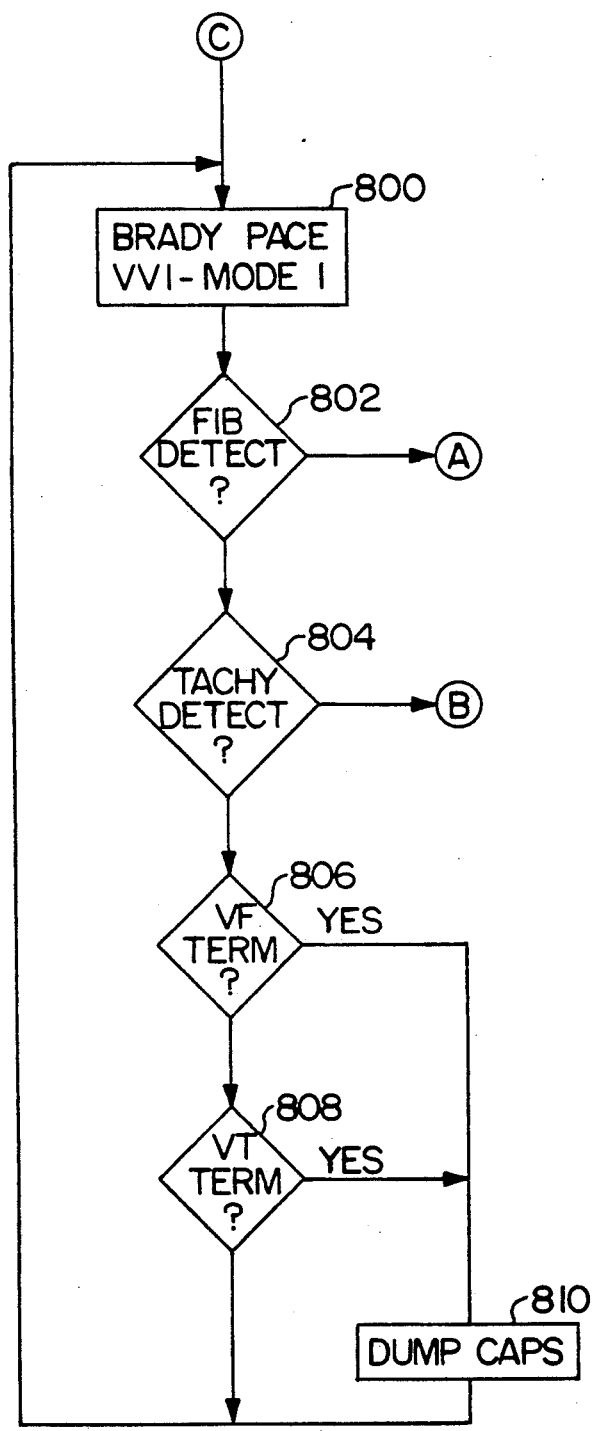
FIGS. 9 through 12 are a functional flow chart, illustrating the overall operation of the synchronization method of the present invention and of an implantable pacemaker/cardioverter/defibrillator embodying the invention.
Figure 10:
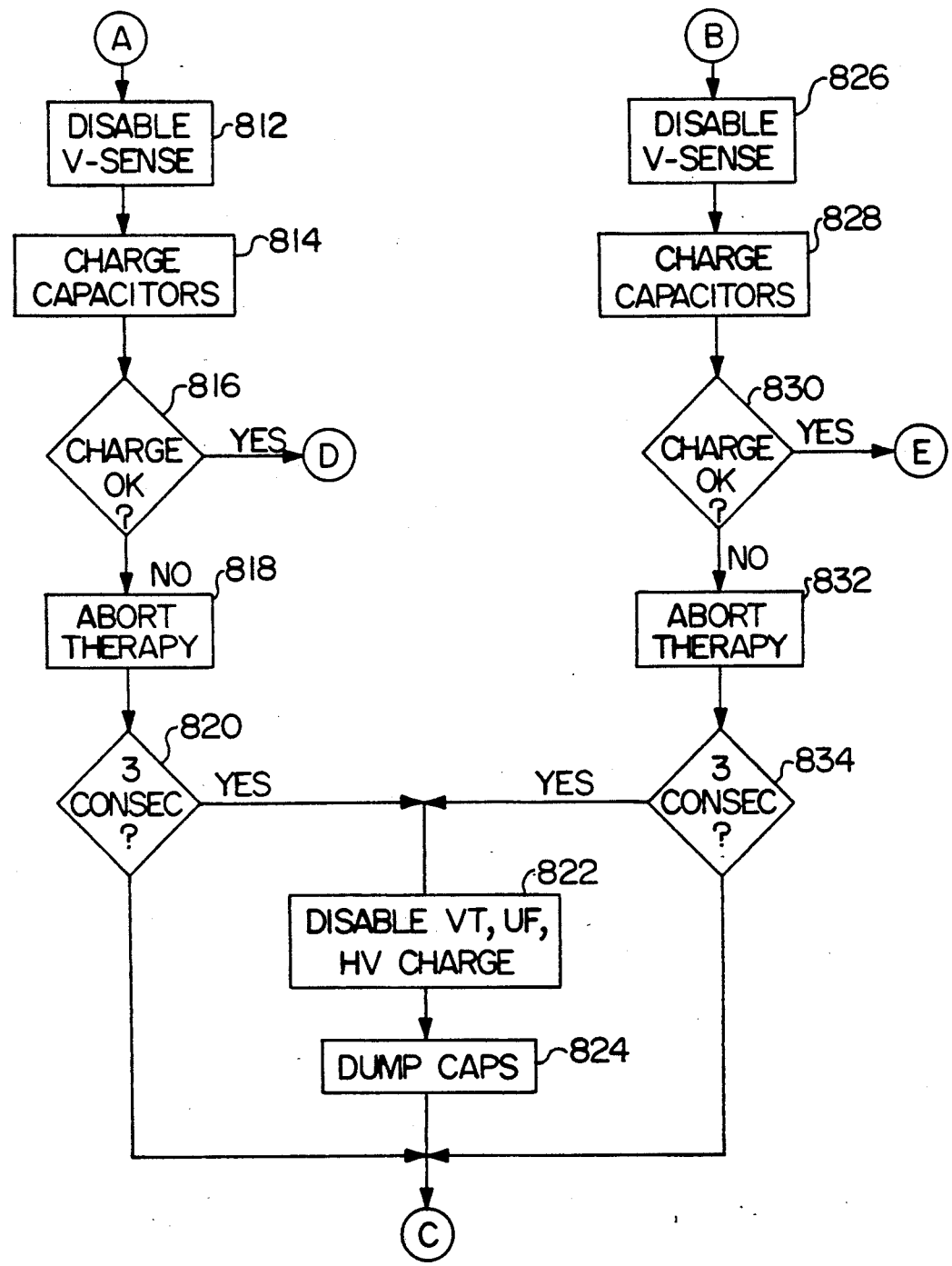

FIG. 9 illustrates the normal operation of the device during bradycardia pacing. Block 800 reflects the fact that the device is executing bradycardia pacing in "Mode 1". For purposes of the present application Mode 1 should be considered to be VVI bradycardia pacing at the programmed parameters. In response to an interrupt indicating occurrence of a pacing pulse or a sensed R-wave, the microprocessor is awakened. Based on the timing of the detected R-wave and/or cardiac pacing pulse, the microprocessor determines whether fibrillation is present at 802. If fibrillation is not present, the microprocessor determines whether tachycardia is present at 804.

Assuming that fibrillation and tachycardia are not found to be present, the microprocessor checks to determine whether fibrillation, if it previously had been detected, has now terminated at 806, and determines whether ventricular tachycardia, if previously detected, has terminated at 808. In the event that termination of fibrillation or tachycardia is detected, the microprocessor triggers control circuitry 4 to cause discharge of the output capacitors 40, 42, 44, and 48 by means of a logic signal on DUMP line 62, and the device continues to function in the programmed bradycardia pacing mode.

In the event that fibrillation or tachycardia is detected, microprocessor 2 will trigger control circuitry 4 to begin charging output capacitors 42, 44, 46 and 48. This portion of the device's operation is illustrated in the flow chart in FIG. 10. In response to detection of a tachycardia, microprocessor 2 disables ventricular sensing by pacer circuitry 10, at 812, and causes control circuitry 4 to initiate charging of the output capacitors at 814. If an excessive period of time passes without the output capacitors reaching the charge level determined by microprocessor 2, as indicated by the signal on VCAP line 64, therapy is aborted at 818. For example, a period of 35 seconds without successful capacitor charging is appropriate in the context of the present invention. In the event that three consecutive attempts to charge the capacitors fail at 820, the microprocessor 2 disables additional charging cycles or VT/VF therapies and may trigger discharge of the output capacitors via a signal on DUMP line 62 from control circuit 4 if desired.

Similarly, after detection of ventricular fibrillation, ventricular sensing is disabled at 826, capacitor charging is initiated at 828, and a determination that the charging has been successful is made at 830. Again, if capacitor charging is unsuccessful, a fibrillation is therapy is aborted at 832, and in response to three consecutive failures to charge, high voltage charging and VT/VF therapies are disabled at 822.

Figure 11:
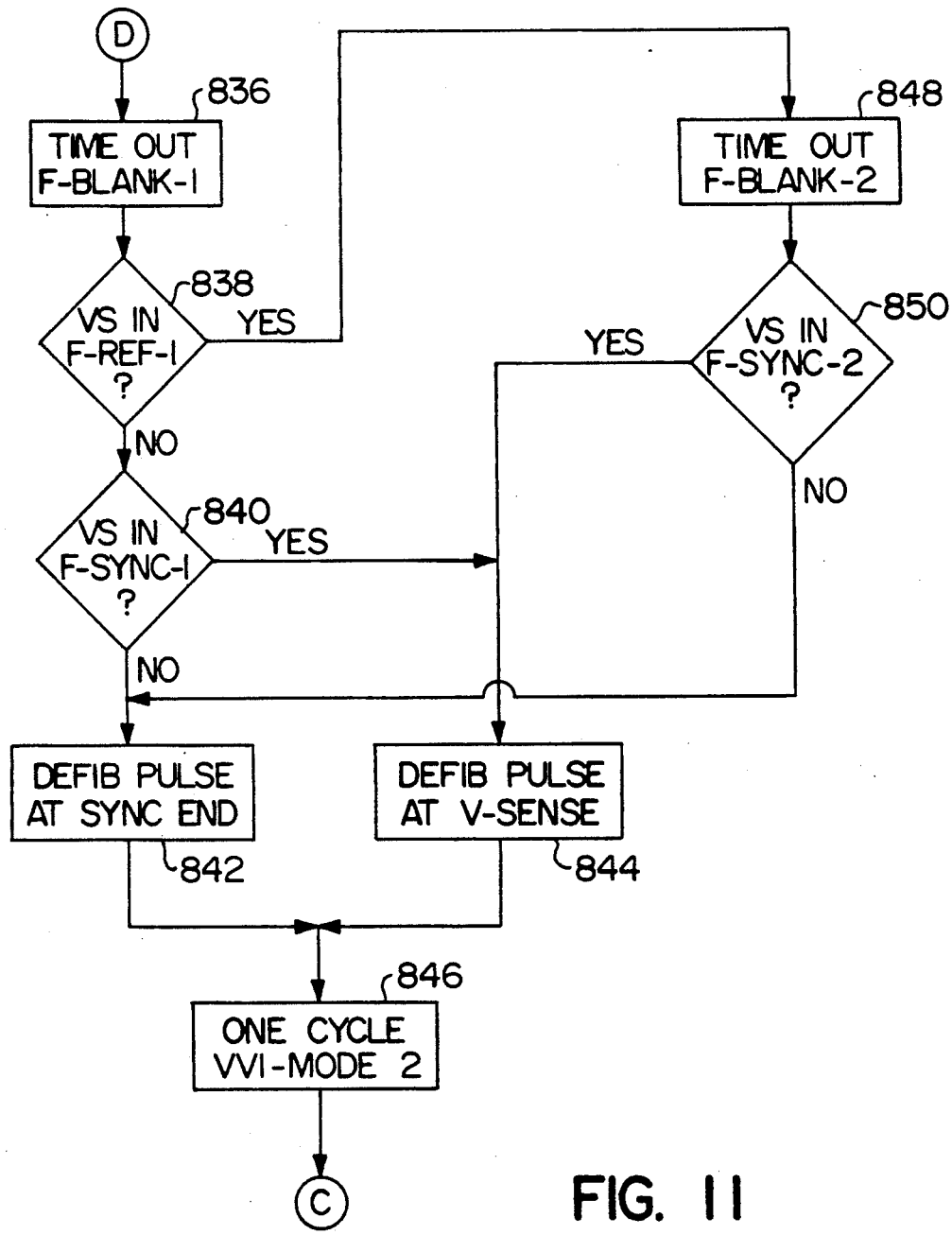

Assuming that capacitor charging is successful, the microprocessor initiates delivery of synchronized cardioversion or defibrillation pulses, as is appropriate. FIG. 11 illustrates the functional operation of the fibrillation synchronization method.

As part of initiation of the synchronization algorithm for fibrillation, the microprocessor employs the timers located within pacer circuitry 10 to define the synchronization, refractory and blanking intervals disclosed above. The timers within pacer circuitry 10 are set to define a first synchronization interval F-SYNC-1, a first refractory interval F-REF-1, and a first blanking interval F-BLANK-1. During time out of F-BLANK-1 at 836, ventricular sensing is disabled. After time out of F-BLANK-1, ventricular sensing is re-enabled by microprocessor 2, which waits for an interrupt indicating the occurrence of ventricular sensing during F-REF-1 at 838. If no interrupt is provided, the microprocessor continues to wait for an interrupt is during the post-refractory portion of F-SYNC-1.

If no R-wave interrupt is received, microprocessor 2 triggers control circuitry 4 to provide a defibrillation pulse at the end of F-SYNC-1, at 842. After delivery of the defibrillation pulse, microprocessor 2 sets the timers in pacer circuitry 10 to define a single cycle of VVI bradycardia pacing in Mode 2, having pre-set blanking, refractory and escape intervals which may be different from those already programmed. For example, in the common text of the present invention, Mode 2 may employ an escape interval of one second, a refractory interval of 520 ms. and a blanking interval of 300 ms. After one cycle of VVI pacing with these pre-set parameters, the microprocessor initiates brady at the programmed parameters, and returns to its bradycardia pacing function as illustrated in FIG. 9. It should be noted that any residual voltage remaining on the output capacitors at this point is not discharged until detection of fibrillation termination at 806 or tachy termination at 808 (FIG. 9).

In the event that an R-wave interrupt occurs during the post-refractory portion of F-SYNC-1, as indicated at 840, microprocessor 2 triggers control circuitry 4 to cause generation of a defibrillation pulse synchronized from the R-wave interrupt, so that the defibrillation pulse is generated during the sensed R-wave. After generation of the defibrillation pulse, the microprocessor specifies one cycle of VVI bradycardia pacing in Mode 2 at 846, as discussed above.

It is believed that an R-wave sensed during the refractory period may be caused by noise or the trailing edge of an R-wave. The intent of the present synchronization method is to synchronize with the leading edge of the R-wave, therefore, in the event that an R-wave is sensed during F-REF-1, the second synchronization interval is initiated, and microprocessor 2 employs the timers in pacer circuitry 10 to define a second synchronization interval F-SYNC-2 and a second blanking interval F-BLANK-2. Timing of intervals associated with the first synchronization period terminates. During F-BLANK-2 at 848, ventricular sensing is disabled. Following time out of F-BLANK-2, the microprocessor 2 awaits for the occurrence of an R-wave-interrupt. If an R-wave interrupt occurs prior to expiration of F-SYNC-2, a defibrillation pulse is triggered synchronized from the R-wave interrupt at 844. If no R-wave interrupt occurs prior to the expiration of F-SYNC-2, a defibrillation pulse is triggered at the expiration of F-SYNC-2 at 842.

This synchronization method assures that the defibrillation pulse is delivered no later than an interval equaled to F-SYNC-2 plus F-REF-1, following charge of the output capacitors. Initiation of the second synchronization interval following sensing in F-REF-1 is believed valuable because it is believed that the delay in pulse delivery associated with the second synchronization interval is more than offset by the potential benefits of delivery of a synchronized defibrillation pulse. However, after failure to synchronize during the second interval, further attempts to synchronization are abandoned, and an asynchronous defibrillation pulse is generated.

Figure 12:
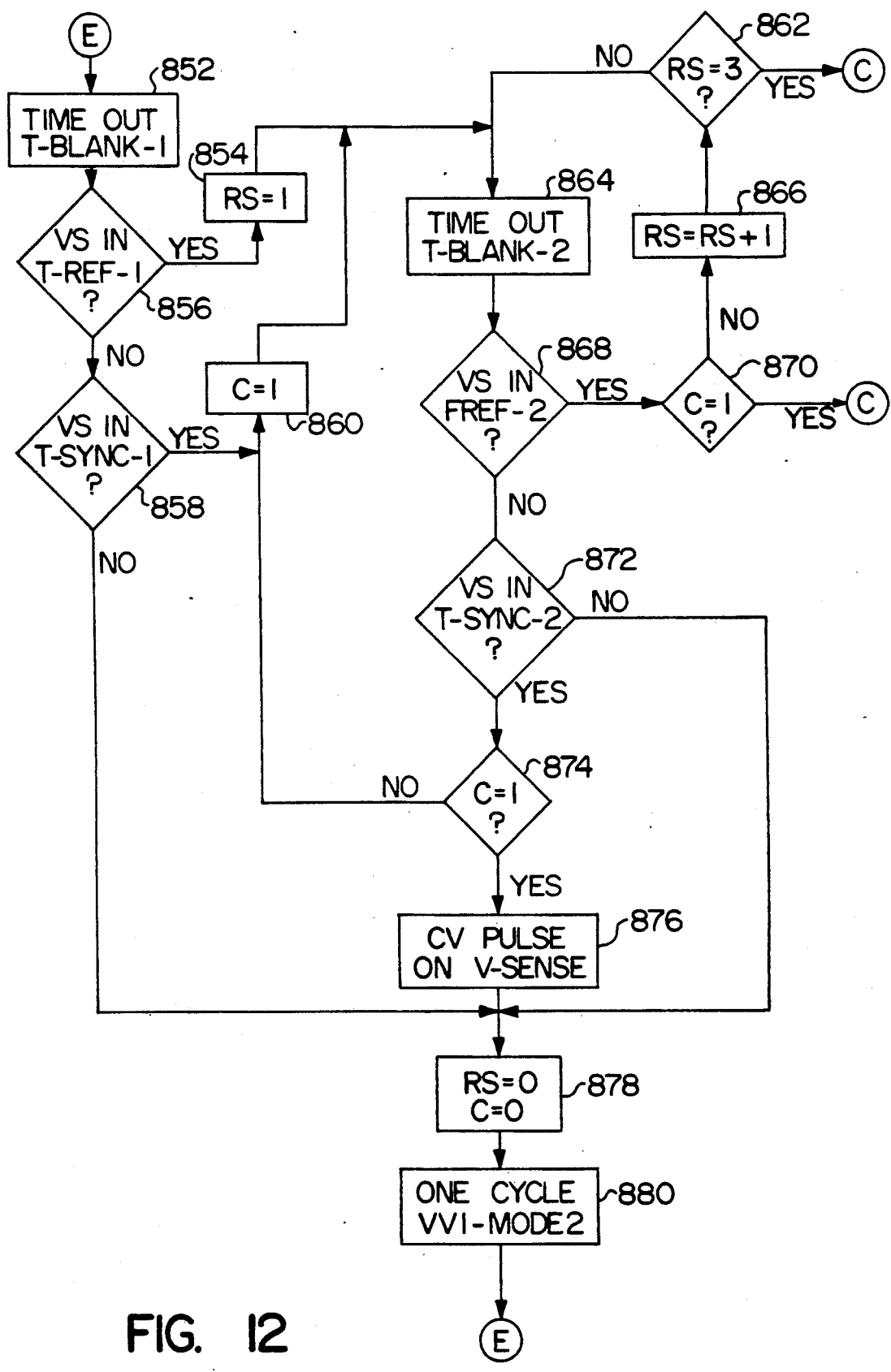

FIG. 12 illustrates the functional operation of the tachycardia synchronization method of the present invention. In performing this method, the microprocessor 2 similarly employs timers within pacer circuitry 10 to define synchronization intervals as discussed above. Following detection of ventricular tachycardia and successful charging of the output capacitors, microprocessor 2 sets the timers in pacer circuitry 10 to define a first synchronization interval T-SYNC-1, a first refractory interval T-REF-1 and a first blanking interval T-BLANK-1. During T-BLANK-1 at 852, ventricular sensing is disabled. In response to an interrupt indicating ventricular sensing during T-REF-1 at 856, the microprocessor 2 notes the occurrence of the refractory sense at 854, and initiates timing of a second synchronization interval T-SYNC-2, a second refractory interval T-REF-2 and a second blanking interval T-BLANK-2.

In the event that no interrupt indicating the occurrence of ventricular sensing occurs during T-REF-1, the microprocessor continues to wait for the occurrence of an interrupt indicating ventricular sensing during T-SYNC-1. If an interrupt occurs, the microprocessor 2 notes it at 860, and initiates the second synchronization interval, as discussed above. In the absence of sensed events occurring during T-SYNC-1, the microprocessor 2 resets any internal flags set at 878, and initiates VVI bradycardia pacing for one cycle in Mode 2 at 880, as discussed above. After an initial cycle of bradycardia pacing in mode 2, the microprocessor returns the function of the device to the programmed bradycardia pacing mode, as illustrated in FIG. 9.

In the event that a second synchronization interval is initiated, the microprocessor 2 waits for an interrupt during T-REF-2 indicative of ventricular sensing. If such an interrupt occurs at 868, the microprocessor checks to determine whether an internal flag (C=1) has been set at 870 indicative of previous sensing during the post-refractory portion of T-SYNC-1. If this flag has been set, microprocessor 2 returns the operation of the device directly to the programmed VVI brady pacing mode 1. If the flag has not been set at 870, the microprocessor increments the count (RS) of sensed events occurring during refractory periods at 866, and checks to see whether three successive refractory sense events have occurred at 868. In the presence of three refractory sense events (that is, R-wave interrupts occurring during the refractory intervals of three successive synchronization intervals) the microprocessor directly returns the operation of the device to the programmed VVI bradycardia pacing mode, and sets the timers in pacer circuitry 10 to define the programmed escape interval, refractory interval and blanking interval normally in effect following delivery of bradycardia pacing pulses.

Assuming that the occurrence of three successive R-wave interrupts during refractory intervals has not occurred, microprocessor 2 initiates timing of a third synchronization interval, having the same parameters as the second synchronization interval. In the event that no R-waves are sensed during T-REF-2, the microprocessor 2 continues to wait, for an interrupt indicating the occurrence of an R-wave during the post-refractory portion of T-SYNC-2, at 872. In the event that no such R-wave is sensed, the microprocessor 2 resets all internal flags at 878, and triggers a single cycle of VVI bradycardia pacing in Mode 2 at 880, and thereafter re-initiates VVI bradycardia pacing at the programmed parameters.

In the event that the microprocessor 2 receives an interrupt indicating the occurrence of an R-wave during T-SYNC-2 at 872, the microprocessor checks at 874 to determine whether a previous R-wave has been sensed in the post-refractory portion of a synchronization interval at 874. If an R-wave previously has been sensed in the post-refractory portion of a synchronization interval, the microprocessor 2 initiates delivery of a cardioversion pulse synchronized to the most recent R-wave interrupt, closely enough coupled so that it occurs during the sensed R-wave, at 876. Microprocessor 2 then resets all internal flags at 878, triggers one cycle of VVI bradycardia pacing in mode 2 at 880, and then returns to programmed bradycardia pacing as illustrated in FIG. 9.

In the event that an R-wave is sensed during the post-refractory portion of T-SYNC-2 at 872, but there is no internal flag set indicating the occurrence of a previous post-refractory sensed R-wave at 874, the microprocessor sets C=1 and initiates timing of the third synchronization interval, employing the same time parameters as the second synchronization interval.

The microprocessor 2 continues to define synchronization intervals having the time parameters of the second synchronization interval until either one of the synchronization intervals expires without ventricular sensing, three R-waves occur within refractory intervals within synchronization intervals, or two R-waves are sensed during the non-refractory portions of successive synchronization intervals. In all cases three synchronization intervals will be adequate in order to determine whether a synchronous cardioversion pulse is delivered.

Figure 4:
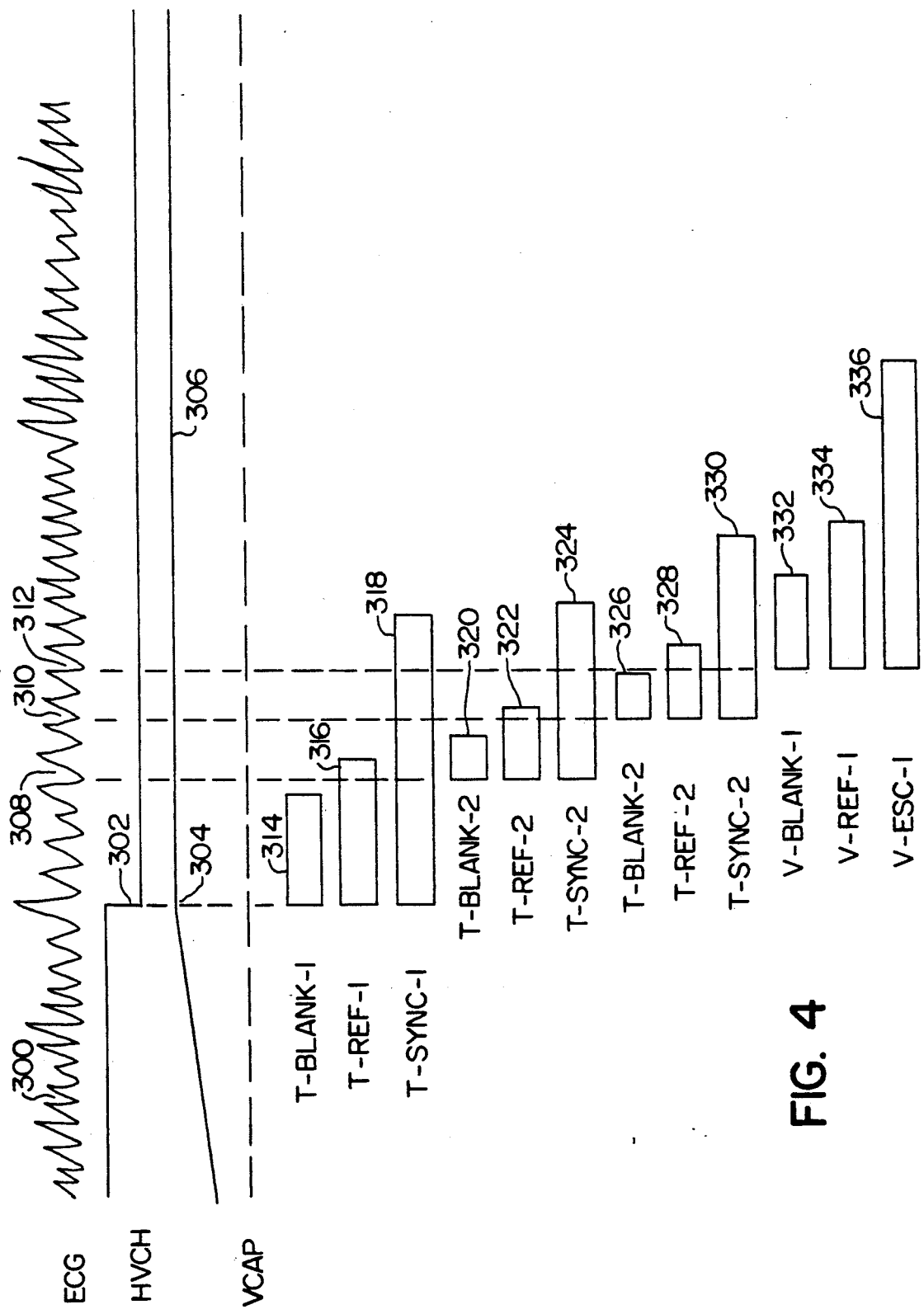
Figure 5:
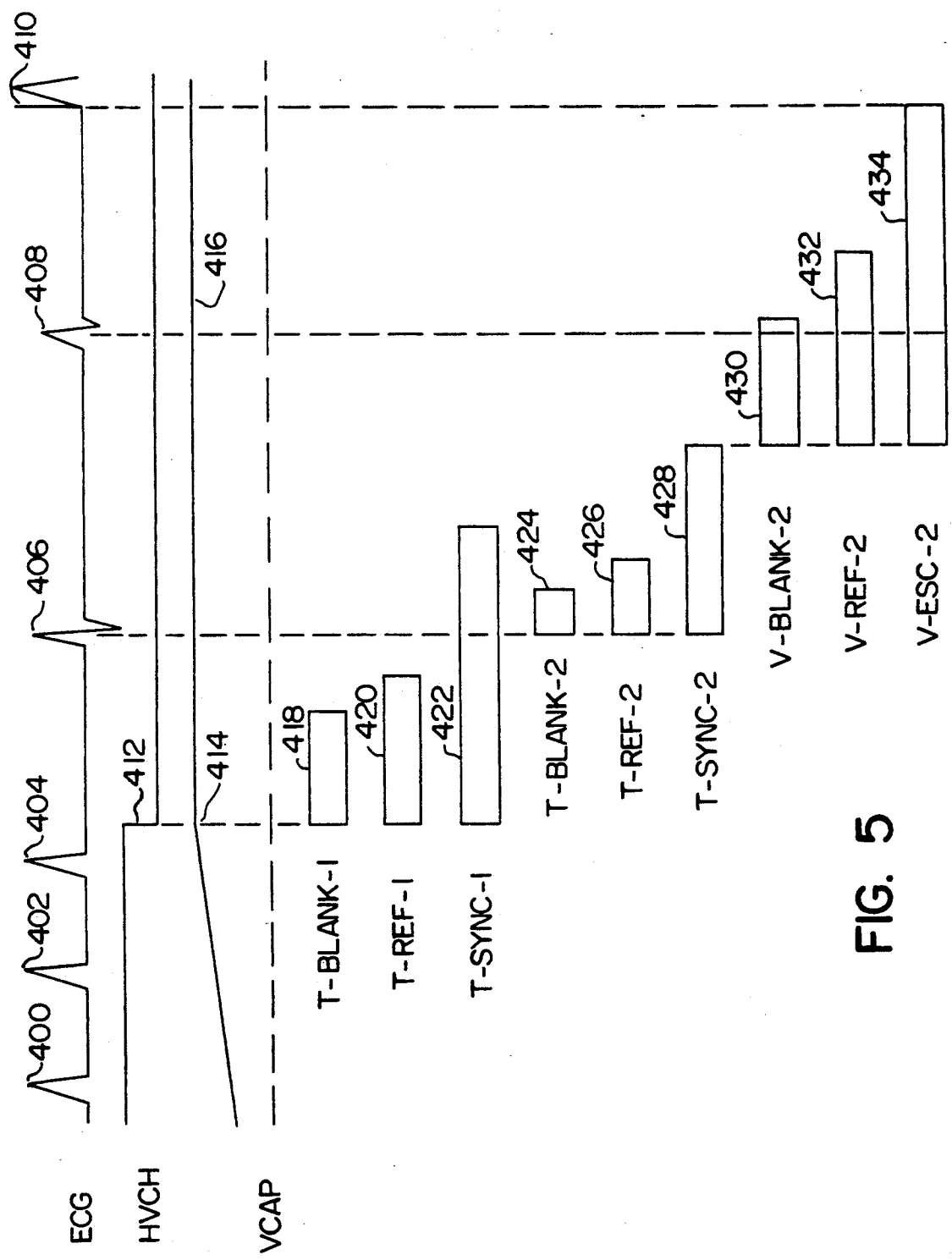
Figure 6:
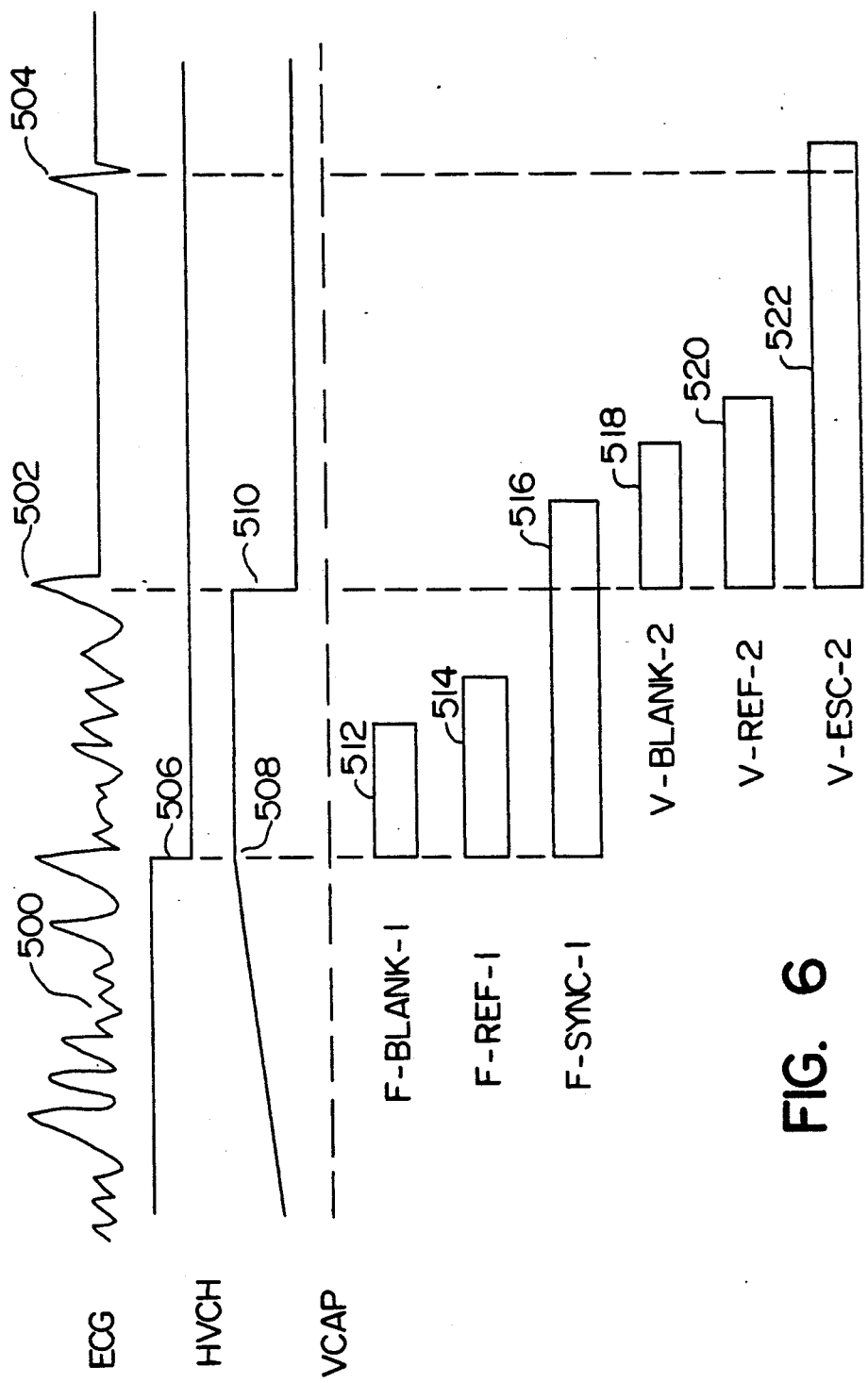
FIGS. 6 through 8 illustrate the operation of a device embodying the synchronization method of the present invention in various circumstances following detection of ventricular fibrillation.
Figure 7:
Figure 8:

Exemplary simulated EKGs and associated timing diagrams are set forth in FIGS. 2 through 8, illustrating the operation of the synchronization method. FIGS. 2 through 5 illustrate the synchronization method employed following detection of tachycardia and successful output capacitor charging. FIGS. 6 through 8 illustrate the method of synchronization after detection of fibrillation and successful output capacitor charging.

Figure 2:
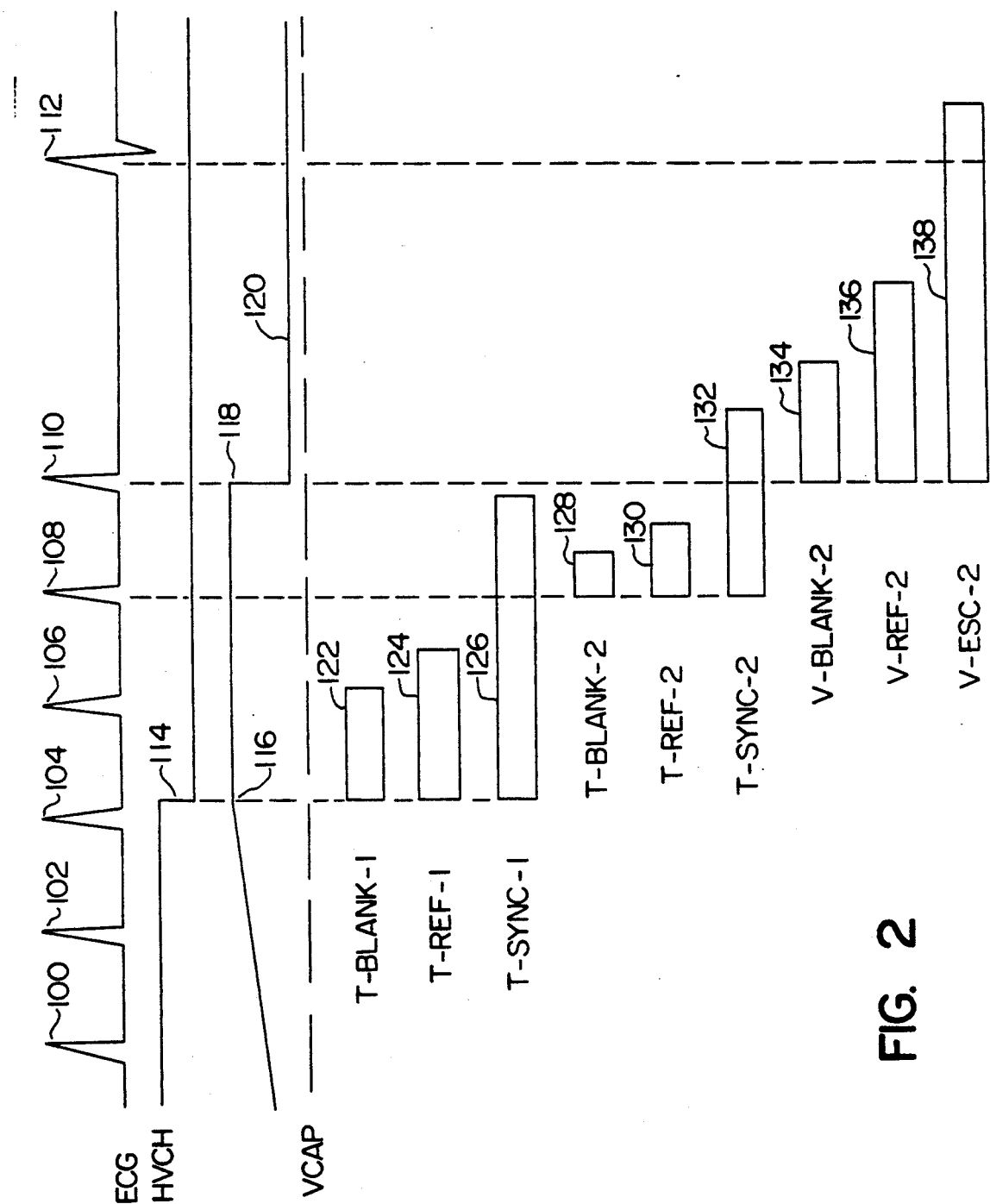
FIGS. 2 through 5 are timing diagrams illustrating the operation of a device embodying the synchronization method of the present invention, in various circumstances following detection of ventricular tachycardia.

FIG. 2 shows an simulated ECG strip, evidencing a ventricular tachycardia indicated by closely spaced R-waves 100, 102, 104, 106, 108 and 110. It is assumed that microprocessor 2 has already detected the occurrence of this tachyarrhythmia, and has enabled control circuitry 4 to initiate charging of the output capacitors by means of a high logic signal on HVCH line 54. At point 116, the voltage on VCAP line 64 reaches the programmed voltage, and HVCH line 54 goes low at 114, terminating the charging process. Following the charging process, an initial blanking interval T-BLANK-1, 122, is defined. An appropriate duration for this blanking interval can be 300 ms. An initial refractory interval T-REF-1, 124, is also defined. An appropriate duration for this interval may be 400 ms.

An initial synchronization interval T-SYNC-1, 126, is also defined. The duration of this interval is preferably a function of the rate criterion for tachycardia detection. In particular, it is recommended that this interval be equal to the tachycardia detection interval (the R-R interval corresponding to the lower limit of the tachycardia rate detection criterion) plus a predetermined time increment associated with the blanking interval and ringing behavior of the sense amplifier, for example 360 ms.

R-wave 106 occurs during the blanking period 122, and thus has no effect. R-wave 108 occurs during the post-refractory portion of the first synchronization interval 126, and initiates the second synchronization interval 132. A second blanking interval T-BLANK-2, 128, is also initiated. This interval may be, for example, 120 ms., and may correspond to the blanking interval used following ventricular sensing during brady pacing or may be a separately defined value. Also initiated is a second refractory interval T-REF-2, 130, which may be, for example, 200 ms., and again may correspond either to the normal refractory interval employed by the device following sensed ventricular contractions, or may be separately defined.

The second synchronization interval T-SYNC-2, 132, is preferably also a function of the rate criterion as discussed above, and may be, for example, the tachycardia detection interval plus 60 ms. Because R-wave 110 is the second successive R-wave sensed within the post-refractory portion of a synchronization interval, it triggers delivery of a cardioversion pulse at 118, and initiates one cycle of mode 2 VVI bradycardia pacing.

Following generation of the cardioversion pulse at 118, microprocessor 2 initiates a ventricular blanking interval V-BLANK-2, 134, which may be 300 ms., a ventricular refractory interval V-REF-2, 136, which may be 520 ms., and a ventricular escape interval V-ESC-2, 138, which may be 1 second, as discussed above. Following sensing of R-wave 112, the device returns to VVI bradycardia pacing at programmed parameters.

It should be noted that following delivery of the cardioversion pulse at 118, some voltage remains on the capacitors as indicated by a positive voltage on VCAP line 64, at 120. This voltage will not be discharged until detection of tachyarrhythmia termination. As discussed above, microprocessor 2 may detect tachyarrhythmia termination in response the occurrence of a predetermined number of sequential R-R intervals greater than the tachycardia detection interval. Following detection of termination, the output capacitors may be discharged internally as discussed above.

Figure 3:
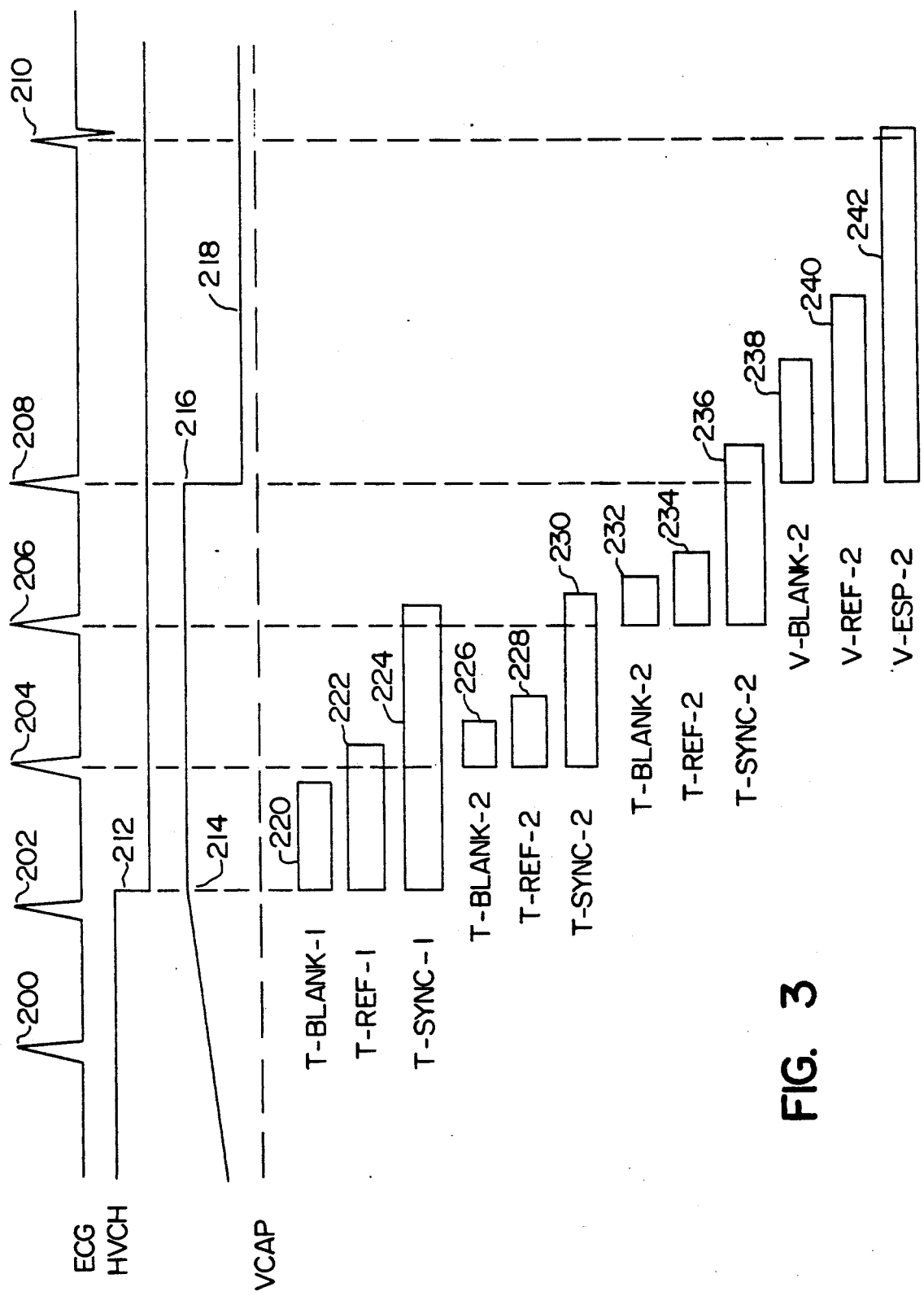

FIGS. 3, 4 and 5 illustrate alternative sequences of events. The time periods indicated in the timing charts correspond to the time intervals discussed in conjunction with FIG. 2, and can be assumed to have identical durations.

FIG. 3 shows an ECG illustrating the occurrence of a ventricular tachycardia as indicated by closely spaced R-waves 200, 202, 204, 206 and 208. Tachycardia is presumed to already have been detected by a high logic signal on HVCH line 54. Upon successful charging of the capacitors at 214, HVCH line 54 goes low at 212, and the first synchronization interval 224, first blanking interval 220, and the first refractory interval 222 are initiated. Because R-wave 204 occurs during the refractory interval 222, a second synchronization interval 230 is initiated, along with blanking interval 226, and refractory interval 228. R-wave 206 occurs during the post-refractory portion of synchronization interval 230, and initiates timing of the third synchronization interval 236, blanking interval 232, and refractory interval 234. R-wave 208 occurs during the post-refractory portion of synchronization interval 236, thus triggering delivery of a cardioversion pulse at 216. Following delivery of the cardioversion pulse at 216, one cycle of VVI pacing in Mode 2 is initiated, and a ventricular blanking interval 238, ventricular refractory interval 240 and ventricular escape interval 242 are specified by microprocessor 2. Following R-wave 210, the device returns to bradycardia pacing at programmed parameters.

FIG. 4 illustrates the occurrence of excessive muscle or other noise 300, rendering synchronization difficult. Again, it is assumed that tachyarrhythmia has already been detected as indicated by a high logic signal on HVCH line 54. Upon successful charging of the output capacitors at 304, HVCH line 54 is set low, and the first synchronization interval 318, the first refractory interval 316 and the first blanking interval 314 are initiated. At 308, an R-wave is detected during the first refractory interval 316, initiating the timing of the second synchronization interval 324, the second refractory interval 322 and the second blanking interval 320. Again, an R-wave is sensed at 310, during refractory interval 322. This in turn initiates the third synchronization interval 330, the third refractory interval 328 and the third blanking interval 326, all of which have durations identical to intervals during the second synchronization interval period at 312. An R-wave occurs during refractory interval 328. Because this is the third R-wave to occur during the refractory portion of the synchronization interval, the microprocessor 2 returns the pacemaker/cardioverter/defibrillator directly to bradycardia pacing, at its programmed parameters. In this case, the first pacing cycle employs a ventricular blanking interval V-BLANK-1, 322, equal to the blanking interval normally employed during VVI pacing, following a pacing pulse. A ventricular refractory period V-REF-1, 334, is similarly defined, corresponding to the refractory period normally used following ventricular pacing. A ventricular escape interval V-ESC-1, 136 is similarly defined, corresponding to the normal, programmed escape interval used during VVI bradycardia pacing. From this point on, bradycardia pacing at programmed parameters continues until redetection of tachyarrhythmia or detection of fibrillation. It should be noted that the output capacitors remain charged, at 306, until detection of tachyarrhythmia termination.

FIG. 5 illustrates the operation of the synchronization method in conjunction with a spontaneous reversion to normal sinus rhythm, after detection of tachycardia. The simulated EKG strip shows a series of tachycardic beats 400, 402, 404 followed by reversion to normal sinus rhythm as indicated by spontaneous heart beats 406 and 408. Again, it is assumed that tachycardia has previously been detected and charging of the output capacitors has already been initiated. On the capacitor reaching its programmed output voltage 414, HVCH line 54 goes low, and the first synchronization interval 422 is initiated, along with the first refractory interval 420 and first blanking interval 418. R-wave 406 occurs during the post-refractory portion of synchronization interval 422, and initiates timing of the second synchronization interval 428 and associated refractory interval 426 and blanking interval 424.

Because no R-waves are sensed during synchronization interval 428, the microprocessor cancels the scheduled cardioversion therapy, and returns the operation of the pacemaker/cardioverter/defibrillator to VVI brady pacing in mode 2, initiating a ventricular blanking period 430, ventricular refractory period 432 and ventricular escape interval 434 . Because spontaneous R-wave 408 occurs during blanking interval 430, it has no effect on the operation of the device. At the expiration of the ventricular escape period 434, a ventricular pacing pulse 410 is triggered. Following this, the microprocessor 2 returns the device to VVI bradycardia at programmed parameters.

It should be noted that the output capacitors are not discharged in response to cancellation of the cardioversion therapy, but are instead maintained in their charged condition, as indicated at 416 and 306 in FIG. 4, until subsequent detection of tachycardia termination.

FIG. 6 illustrates the operation of the synchronization method following detection of fibrillation. The simulated EKG illustrates ventricular fibrillation at 500. At 508, the output capacitors are successfully charged as indicated by return of HVCH line 54 to a low logic level at 506, and the first synchronization interval 516 is initiated. For purposes of synchronization following fibrillation detection, the first synchronization interval F-SYNC-1 may be a pre-set duration, for example 800 ms., or may be a function of the tachycardia detection interval. For example, at the duration of F-SYNC-1 may be set equal to the tachycardia detection interval plus 360 ms., as discussed in conjunction with the determination of the initial tachycardia synchronization interval T-SYNC-1. The initial blanking interval F-BLANK-1, 512, may be set at 300 ms. and the initial refractory interval F-REF-1, 514, may be set at 400 ms. An R-wave is detected at 502, within the post-refractory portion of F-SYNC-1, 516, triggering delivery of a defibrillation pulse at 510.

The microprocessor 2 then returns the device to VVI bradycardia pacing mode 2, for one cycle, defining a ventricular escape interval 522, ventricular refractory period 520 and ventricular blanking period 518 corresponding to similarly labeled V-BLANK-2, V-REF-2 and V-ESC-2 intervals in FIGS. 2 through 5. A spontaneous R-wave 504 occurs during V-ESC-2, 522, and after this R-wave, the device returns to VVI bradycardia pacing at programmed parameters.

FIG. 7 includes a simulated ECG indicative of ventricular fibrillation 600. After successful charging of the output capacitors at 610, indicated by the return of HVCH line 54 to a low logic state at 606, the first synchronization interval F-SYNC-1, 620 is initiated, with refractory interval F-REF-1, 618, and blanking interval F-BLANK-1, 616, corresponding to those discussed in conjunction with FIG. 6. An R-wave is sensed at 602, during refractory period 618, initiating timing of the second synchronization interval F-SYNC-2, 624, and a second blanking interval F-BLANK-2, 622. The duration of F-SYNC-2 may correspond to the duration of the second synchronization interval T-SYNC-2, discussed above, based on the selected tachycardia detection interval, or may be a fixed interval. The duration of F-BLANK-2 can correspond to the normal blanking period following sensed ventricular contractions used during VVI pacing (e.g. 120 ms.), or may be a predetermined different fixed value.

A second R-wave is detected at 604, which occurs during the post-blanking portion of the second synchronization interval F-SYNC-2, 624, triggering delivery of a defibrillation pulse at 612. Following delivery of the defibrillation pulse, the microprocessor 2 initiates a single cycle of VVI pacing in Mode 2, initiating an escape interval 630, a refractory interval 628 and a blanking interval 626 corresponding to similarly labeled intervals in previous timing charts. Spontaneous R-wave 614 occurs during escape interval 630, inhibiting delivery of a cardiac pacing pulse. Following R-wave 614, microprocessor 2 returns the operation of the device to VVI bradycardia pacing at the programmed parameters.

It should be noted that the residual voltage 632 remaining on the output capacitors remains until detection of fibrillation termination. Fibrillation termination detection can be accomplished, for example, by detection of a predetermined number of R-R intervals all having durations greater than a predetermined fibrillation detection interval, equal to the R-R interval corresponding to the rate required for fibrillation detection.

FIG. 8 illustrates the operation of the defibrillation synchronization method when it is impossible to deliver a synchronized defibrillation pulse. The simulated ECG illustrates a pattern 700 indicative of ventricular fibrillation. Upon successful charging of the output capacitors at 706, as indicated by the logic level on HVCH line 54 going low at 74, the first synchronization interval 716 is initiated, along with corresponding blanking and refractory intervals 712 and 714. Because no R-wave is sensed during synchronization interval 716, a defibrillation pulse is triggered at the expiration of synchronization interval 716, at 708. The microprocessor 2 then returns the device to VVI bradycardia pacing for one cycle in mode 2, with corresponding defined escape interval 722, refractory period 720 and blanking interval 718, corresponding to the intervals discussed previously in conjunction with ventricular pacing in mode 2. At expiration of escape interval 722, a ventricular pacing pulse 702 is generated, and the device thereafter performs VVI bradycardia pacing at the programmed parameters, pending redetection of fibrillation or tachycardia detection. The residual voltage 710 remaining on the output capacitors remains until detection of fibrillation termination.

The above specification discloses a ventricular cardioverter/defibrillator. However, the invention described is also believed valuable in the context of an atrial cardioverter or defibrillator. Similarly, the synchronization method is disclosed in conjunction with a number of preferentially defined time intervals. However, variation in these time intervals should be expected, particularly in conjunction with variation in the intervals defining the tachycardia and fibrillation detection criteria of the pacemaker/cardioverter/defibrillator in which the invention is practiced. Similarly, particular criteria are set forth with regard to detection of tachycardia termination as a prerequisite for internal discharge of the output capacitors. Other criteria may readily be substituted for these specific criteria, keeping in mind that the value of retaining the charge after an aborted therapy depends on the termination detection criteria being more stringent than the criteria for aborting the scheduled cardioversion therapy. Similarly, the described device allocates functional elements to particular portions and types of circuitry, employing a conventional division between a microprocessor and external timing and control circuitry. However, the device is also readily practiced in conjunction with other microprocessor based implementations, and may also be practiced in implementations employing full custom digital circuitry or analog circuitry to perform control and timing functions. As such, the above disclosure should be considered exemplary, rather than limiting with regard to the claims that follow.

In conjunction with the above disclosure, I claim:

1. In a cardiovertor/defibrillator comprising means for detecting fibrillation, means for detecting tachyarrhythmia and means for generating high energy cardioversion and defibrillation pulses, including capacitor means and means for charging said capacitor means upon detection of a tachyarrhythmia by said tachyarrhythmia detecting means, for delivery to the heart, the improvement comprising:

defibrillation pulse synchronization means for triggering said pulse generating means to deliver a defibrillation pulse in response to detection of fibrillation by said fibrillation detecting means, said defibrillation pulse synchronization means comprising means for sensing heart rhythm, means for defining a first set of requirements for said heart rhythm and means for triggering delivery of said defibrillation pulse when said first set of requirements are met; and cardioversion pulse synchronization means for triggering said pulse generating means to deliver a cardioversion pulse in response to detection of tachyarrhythmia by said tachyarrhythmia detecting means, said cardioversion pulse synchronization means comprising means for sensing heart rhythm, means for defining a second set of requirements differing from said first set of requirements, and means for triggering delivery of said cardioversion pulse when said second set of requirements are met, wherein said cardioversion pulse synchronization means comprises:

means for defining at least two synchronization intervals following charging of said capacitor means;

means for detecting of R-waves during said synchronization intervals; and triggering means responsive to the detection of R-waves during two successive ones of said synchronization intervals for triggering delivery of said cardioversion pulse synchronized to the detection of said R-wave during the second of said two successive synchronization intervals.

2. In a cardiovertor/defibrillator comprising means for detecting fibrillation, means for detecting tachyarrhythmia and means for generating high energy cardioversion and defibrillation pulses, including capacitor means and means for charging said capacitor means upon detection of a tachyarrhythmia by said tachyarrhythmia detecting means, for delivery to the heart the improvement comprising:

defibrillation pulse synchronization means for triggering said pulse generating means to delivery a defibrillation pulse in response to detection of fibrillation by said fibrillation detecting means, said defibrillation pulse synchronization means comprising means for sensing heart rhythm, means for defining a first set of requirements for said heart rhythm and means for triggering delivery of said defibrillation pulse when said first set of requirements are met; and cardioversion pulse synchronization means for triggering said pulse generating means to deliver a cardioversion pulse in response to detection of tachyarrhythmia by said tachyarrhythmia detecting means, said cardioversion pulse synchronization means comprising means for sensing heart rhythm, means for defining a second set of requirements for said heart rhythm differing from said first set of requirements, and means for triggering delivery of said cardioversion pulse when said second set of requirements are met; and wherein said defibrillation pulse synchronization means comprises:

means for defining at least one synchronization interval following charging of said capacitor means;

means for detecting the occurrence of an R-wave during said at least one synchronization interval;

means responsive to the detection of an R-wave during said synchronization interval for triggering the synchronized delivery of said defibrillation pulse; and means for triggering the delivery of said defibrillation pulse at the expiration of said synchronization interval in the absence of the detection of an R-wave during said synchronization interval.

3. In a cardioverter comprising means for detection of heart rhythm, means for defining detection requirements for said heart rhythm, means for detection of an arrhythmia when said heart rhythm meets said detection requirements, output capacitor means for generating high energy pulses for delivery to the heart to terminate said arrhythmia, and means for charging said output capacitor means in response to detection of said arrhythmia; the improvement comprising:

pulse synchronization means for triggering said pulse generating means to deliver a cardioversion pulse in response to detection of said arrhythmia by said detection means, said synchronization means comprising: means for verifying the continued presence of said detected arrhythmia after charging of said capacitor means and for aborting the delivery of said high energy pulse unless the continuing presence of said arrhythmia is verified; means for detecting the termination of said detected arrhythmia after charging of said capacitor means; and means for retaining the charge on said capacitor means until the detection of the termination of said arrhythmia and for discharging the charge on said capacitor means in response to the detection of the termination of said detected tachyarrhythmia.

4. A cardioverter according to claim 3 wherein said verifying means comprises: means for defining at least two synchronization intervals following charging of said capacitor means; means for detection of R-waves during said synchronization intervals; and means responsive to the detection of R-waves during two successive ones of said synchronization intervals for triggering delivery of said high energy pulse synchronized to the detection of said R-wave during the second of said two successive synchronization intervals.

5. A cardioverter according to claim 4 wherein said verifying means comprises means responsive to the failure to detect an R-wave during any one of said synchronization intervals for aborting the delivery of said high energy pulse.

6. In a defibrillator comprising means for detection of heart rhythm, means for defining detection requirements for said heart rhythm, means for detection of fibrillation when said heart rhythm meets said detection requirements, output capacitor means for generating high energy defibrillation pulses for delivery to the heart, and means for charging said output capacitor means in response to detection of fibrillation; the improvement comprising:

defibrillation pulse synchronization means for triggering said pulse generating means to deliver a defibrillation pulse in response to detection of fibrillation by said fibrillation detection means, said fibrillation synchronization means comprising: means for defining at least one synchronization interval following charging of said capacitor means; means for detecting the occurrence of an R-wave during said at least one synchronization interval; triggering means responsive to the detection of an R-wave during a predetermined portion of said synchronization interval for triggering the synchronized delivery of said defibrillation pulse; and means for triggering the delivery of said defibrillation pulse at the expiration of said synchronization interval in the absence of the occurrence of an R-wave during said synchronization interval.

7. A defibrillator according to claim 6 wherein said defining means comprises means for defining two synchronization intervals and wherein the first of said synchronization intervals further comprises a refractory interval, wherein said defining means is responsive to the detection of an R-wave during said refractory interval for initiating the second of said synchronization intervals and wherein said triggering means is responsive to the detection of an R-wave during either of said synchronization intervals.

8. In a cardioverter comprising means for detection of heart rhythm, means for defining detection requirements for said heart rhythm, means for detection of an arrhythmia when said heart rhythm meets said detection requirements, output capacitor means for generating high energy pulses for delivery to the heart to terminate said arrhythmia, and means for charging said output capacitor means in response to detection of said arrhythmia; the improvement comprising:

pulse synchronization means for triggering said pulse generating means to deliver a high energy pulse in response to detection of said arrhythmia by said detection means, said pulse symchronization means comprising: means for defining at least two synchronization intervals following charging of said capacitor means; means for detection of R-waves during said synchronization intervals; and triggering means responsive to the detection of R-waves during predetermined portions of two successive ones of said synchronization intervals for triggering delivery of said high energy pulse synchronized to the detection of said R-wave during the second of said second of said successive synchronization intervals.

9. A cardioverter according to claim 8 wherein said defining means comprises means for defining a refractory interval during the first of said synchronization intervals and wherein said defining means is responsive to the detection of an R-wave during said refractory interval and for initiating the second of said synchronization intervals.

10. A cardioverter according to claim 9 wherein said defining means comprises means for defining at least three synchronization intervals, wherein said defining means comprises means for defining refractory intervals during at least the first two of said synchronization intervals, and wherein said triggering means comprises means responsive to the detection of R-waves in the non-refractory portions of two successive ones of said synchronization intervals for triggering delivery of said high energy pulse.

11. In a cardioverter comprising means for detection of heart rhythm, means for defining detection requirements for said heart rhythm, means for detection of an arrhythmia when said heart rhythm meets said detection requirements, output capacitor means for generating high energy pulses for delivery to the heart to terminate said arrhythmia, and means for charging said output capacitor means in response to detection of said arrhythmia, the improvement comprising:

pulse synchronization means for triggering said pulse generating means to deliver a cardioversion pulse in response to detection of said arrhythmia by said detection means, said synchronization means comprising means for verifying the continued presence of said detected arrhythmia after charging of said capacitor means and for aborting the delivery of said high energy pulse unless the continuing presence of said arrhythmia is verified, said verifying means comprising means for determining whether the rhythm of said heart meets a first set of criteria;

means for detecting the termination of said detected arrhythmia after charging of said capacitor means, said means for detecting the termination of said detected arrhythmia comprising means for determining whether the rhythm of said heart meets second criteria, differing from said first criteria; and means for retaining the charge on said capacitor means, after aborting the delivery of said high energy pulse by said verifying means, until detection of the termination of said arrhythmia and for discharging the charge on said capacitor in response to the detection of the termination of said detected arrhythmia.

12. In a cardioverter/defibrillator comprising means for detecting fibrillation, means for detecting tachyarrhythmia and means for generating high energy cardioversion and defibrillation pulses for delivery to the heart, the improvement comprising:

defibrillation pulse synchronization means for triggering said pulse generating means to delivery a defibrillation pulse in response to detection of fibrillation by said fibrillation detecting means, said defibrillation pulse synchronization means comprising means for defining a synchronization interval following detection of fibrillation by said fibrillation detecting means, means for triggering delivery of said defibrillation pulse synchronized to a depolarization of said heart occurring within said synchronization interval and means for triggering delivery of said defibrillation pulse at the expiration of said synchronization interval, in the absence of an occurrence of a depolarization of said heart during said synchronization interval; and cardioversion pulse synchronization means for triggering said pulse generating means to deliver a cardioversion pulse in response to detection of tachyarrhythmia by said tachyarrhythmia detecting means, said cardioversion pulse synchronization means comprising means for defining a synchronization interval following detection of tachyarrhythmia by said detecting means, means for triggering delivery of a cardioversion pulse synchronized to a depolarization of said heart occurring within said synchronization interval and means for aborting delivery of a cardioversion pulse in response to the absence of a cardiac depolarization during said synchronization interval.

* * * * *